(12) United States Patent
Winnard

(10) Patent No.: US 11,826,895 B2
(45) Date of Patent: Nov. 28, 2023

(54) APPARATUS FOR RELEASABLY HOLDING A SOCKET

(71) Applicant: Standley D. Winnard, Dallas, TX (US)

(72) Inventor: Standley D. Winnard, Dallas, TX (US)

( * ) Notice: Subject to any disclaimer, the term of this patent is extended or adjusted under 35 U.S.C. 154(b) by 0 days.

(21) Appl. No.: 17/377,258

(22) Filed: Jul. 15, 2021

(65) Prior Publication Data

US 2021/0339376 A1 Nov. 4, 2021

Related U.S. Application Data

(63) Continuation of application No. 16/499,783, filed as application No. PCT/US2017/025625 on Mar. 31, 2017, now Pat. No. 11,091,778.

(51) Int. Cl.
| | |
|---|---|
| *B25H 3/00* | (2006.01) |
| *A61K 39/12* | (2006.01) |
| *A61K 39/205* | (2006.01) |
| *A61K 39/215* | (2006.01) |
| *C12N 15/86* | (2006.01) |
| *A61K 39/00* | (2006.01) |

(52) U.S. Cl.
CPC ............ *B25H 3/003* (2013.01); *A61K 39/12* (2013.01); *A61K 39/205* (2013.01); *A61K 39/215* (2013.01); *C12N 15/86* (2013.01); *A61K 2039/5254* (2013.01); *A61K 2039/5256* (2013.01); *C12N 2760/20034* (2013.01); *C12N 2760/20043* (2013.01); *C12N 2760/20134* (2013.01); *C12N 2760/20143* (2013.01); *C12N 2770/20022* (2013.01); *C12N 2770/20034* (2013.01)

(58) Field of Classification Search
CPC ............ B25H 3/003; B25H 3/04; B25H 3/00
USPC .................. 206/378, 373, 372; 211/70.6
See application file for complete search history.

(56) References Cited

U.S. PATENT DOCUMENTS

| | | | | |
|---|---|---|---|---|
| 7,658,284 | B2 * | 2/2010 | Lin ...................... | B25H 3/003 |
| | | | | 221/70 |
| 7,841,480 | B2 * | 11/2010 | Hsieh ..................... | B25H 3/06 |
| | | | | 403/328 |
| 8,336,709 | B1 * | 12/2012 | Geibel .................... | B25H 3/06 |
| | | | | 206/378 |
| 9,205,552 | B2 * | 12/2015 | Kao ..................... | F16M 13/022 |
| 9,527,206 | B1 * | 12/2016 | Hsieh ..................... | B25H 3/04 |
| 9,662,781 | B1 * | 5/2017 | Kao ........................ | B25H 3/003 |
| 9,694,491 | B1 * | 7/2017 | Kao ........................ | B25H 3/003 |
| 9,782,890 | B2 * | 10/2017 | Hsieh ..................... | B25H 3/04 |
| 10,022,857 | B2 * | 7/2018 | Kao ........................ | B25H 3/04 |
| 10,589,416 | B1 * | 3/2020 | Hsieh ..................... | F16B 2/22 |

(Continued)

*Primary Examiner* — Steven A. Reynolds
(74) *Attorney, Agent, or Firm* — Peter V. Schoreder; Booth Albanesi Schroeder PLLC

(57) ABSTRACT

A socket organizer for releasably and adjustably holding socket holders is provided. The organizer has a longitudinally extending rail assembly characterized by a generally U-shaped channel. A plurality of socket holders are positioned in and slidingly engage the channel. Each socket holder has a detent assembly for releasably locking a socket. A plurality of clip members are attached to the rail assembly or to mounting posts. The clip members have socket identification indicia and are positioned over the mounting posts by way of an aperture. A positioning mechanism is provided for selectively positioning individual socket holders in the channel.

17 Claims, 13 Drawing Sheets

(56) References Cited

U.S. PATENT DOCUMENTS

| | | | | |
|---|---|---|---|---|
| 10,792,803 B1* | 10/2020 | Kao | ............... | B25H 3/003 |
| 2004/0211691 A1* | 10/2004 | Winnard | ............... | B25H 3/003 |
| | | | | 206/378 |
| 2005/0218023 A1* | 10/2005 | Winnard | ............... | B25H 3/003 |
| | | | | 206/378 |
| 2005/0221664 A1* | 10/2005 | Winnard | ............... | B25H 3/003 |
| | | | | 439/510 |
| 2011/0089126 A1* | 4/2011 | Hsieh | ............... | B25H 3/06 |
| | | | | 211/70.6 |
| 2016/0096264 A1* | 4/2016 | Kao | ............... | B25H 3/06 |
| | | | | 206/378 |
| 2018/0065792 A1* | 3/2018 | Chen | ............... | B25H 3/003 |
| 2020/0101590 A1* | 4/2020 | Winnard | ............... | C12N 15/86 |

\* cited by examiner

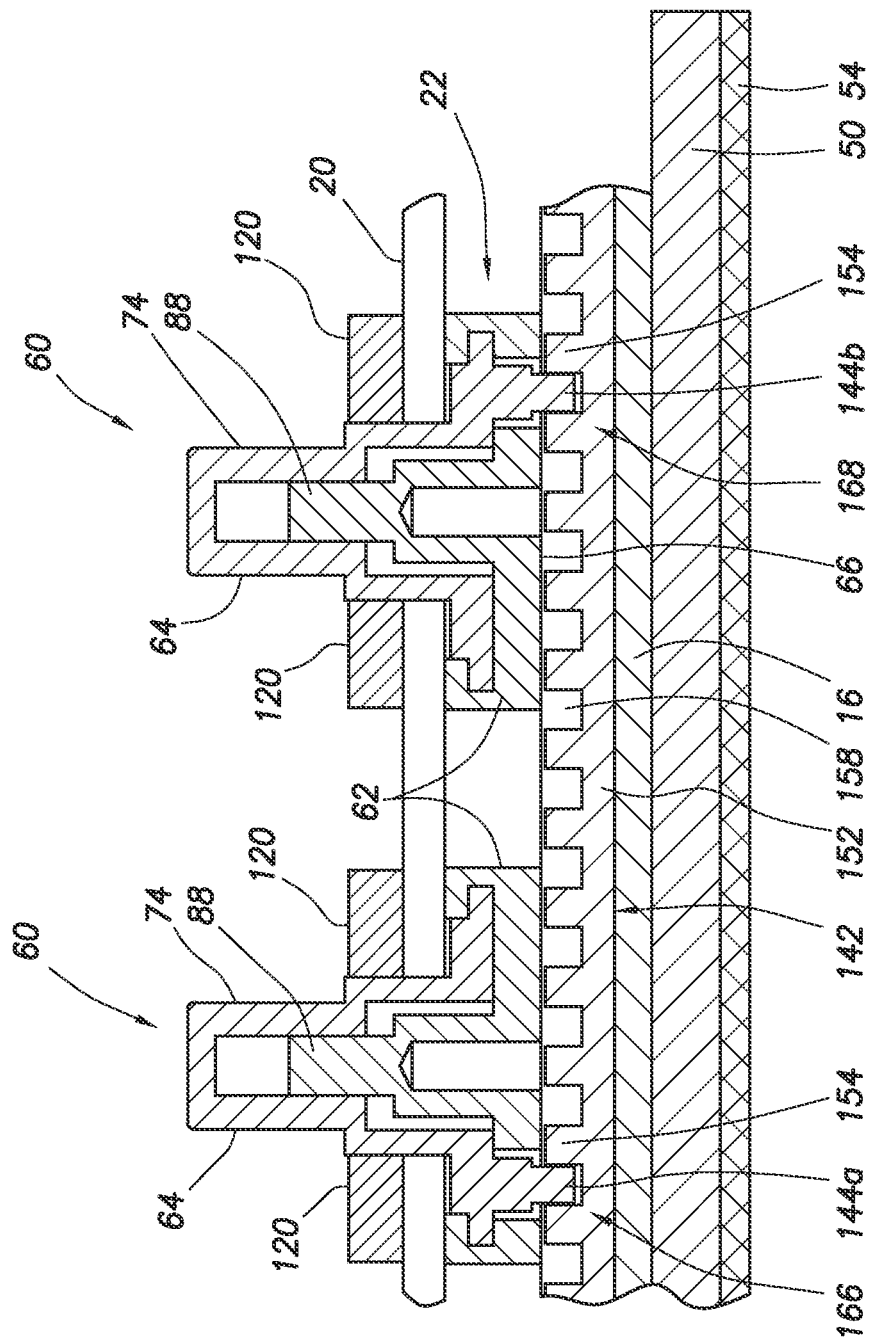

APPARATUS FOR RELEASABLY HOLDING A SOCKET

CROSS-REFERENCE TO RELATED APPLICATIONS

This is a Continuation application claiming priority to U.S. patent application Ser. No. 16/499,783, filed Sep. 30, 2019, which is a National Stage application claiming priority to PCT International Application No. PCT/US17/025625 filed Mar. 31, 2017.

TECHNICAL FIELD

The disclosure relates to releasable hand tool holders and more particularly to an apparatus for securely and releasably holding sockets which can be readily positioned on and removed from the tool holder.

BRIEF DESCRIPTION OF THE DRAWINGS

For a more complete understanding of the present invention, and the advantages thereof, reference is now made to the following description which is to be taken in conjunction with the accompanying drawings in which like reference numerals indicate like parts and wherein:

FIG. 9 is a longitudinal cross-sectional view of the exemplary apparatus of FIG. 7.

DETAILED DESCRIPTION OF THE DISCLOSURE

Socket tools, or simply sockets, are universally used by professional and amateur mechanics and maintenance technicians and come in sets of various size and style. Storing and organizing sockets is a challenge due to their various sizes, shape, and typical numbers in a set. U.S. Pat. No. 6,991,105 to Winnard, issued Jan. 31, 2006, provides further disclosure regarding devices designed to organize and store sockets and is incorporated herein by reference for all purposes.

Commercially available socket holder apparatus typically provide a series of individual socket holders in a straight line configuration along a central rail or tool body. The sockets are attached and released by hand, such as by push-on, pull-off action or by half-turns and the like, from a holding post or similar. The sockets held on the socket holders are in close proximity to one another and adjacent sockets can "rattle" or impact one another, especially during transport of the apparatus in a vehicle. Repeated contact eventually results in damage to adjacent sockets such as flaking chrome or coating, scratches and dents and the like.

Some socket holders are mounted to move along a rail or tool body without any way to secure the socket holders to specific locations. For larger socket sizes, adjacent sockets bang into one another every time the rail or body is tilted sufficiently to cause the holders to slide and when the rail is rotated to or through a generally vertical orientation. Even on an apparatus having a way to secure the socket holders into selected positions, the holders sometimes come loose by accident, vibration, part failure, or wear, resulting in unwanted and damaging rattling or sliding of adjacent sockets into one another. Secure and spaced positioning of adjacent socket holders on a tool holding apparatus to prevent contact between adjacent sockets is needed.

While the sockets are typically marked with identifying information, often by stamping of the exterior surface of the socket cylinder, it can be difficult to read the information, especially where the sockets are positioned in a line where the information can be obscured by adjacent sockets.

Rail System with Socket Holder Assemblies and Clip Members

Figure 1:
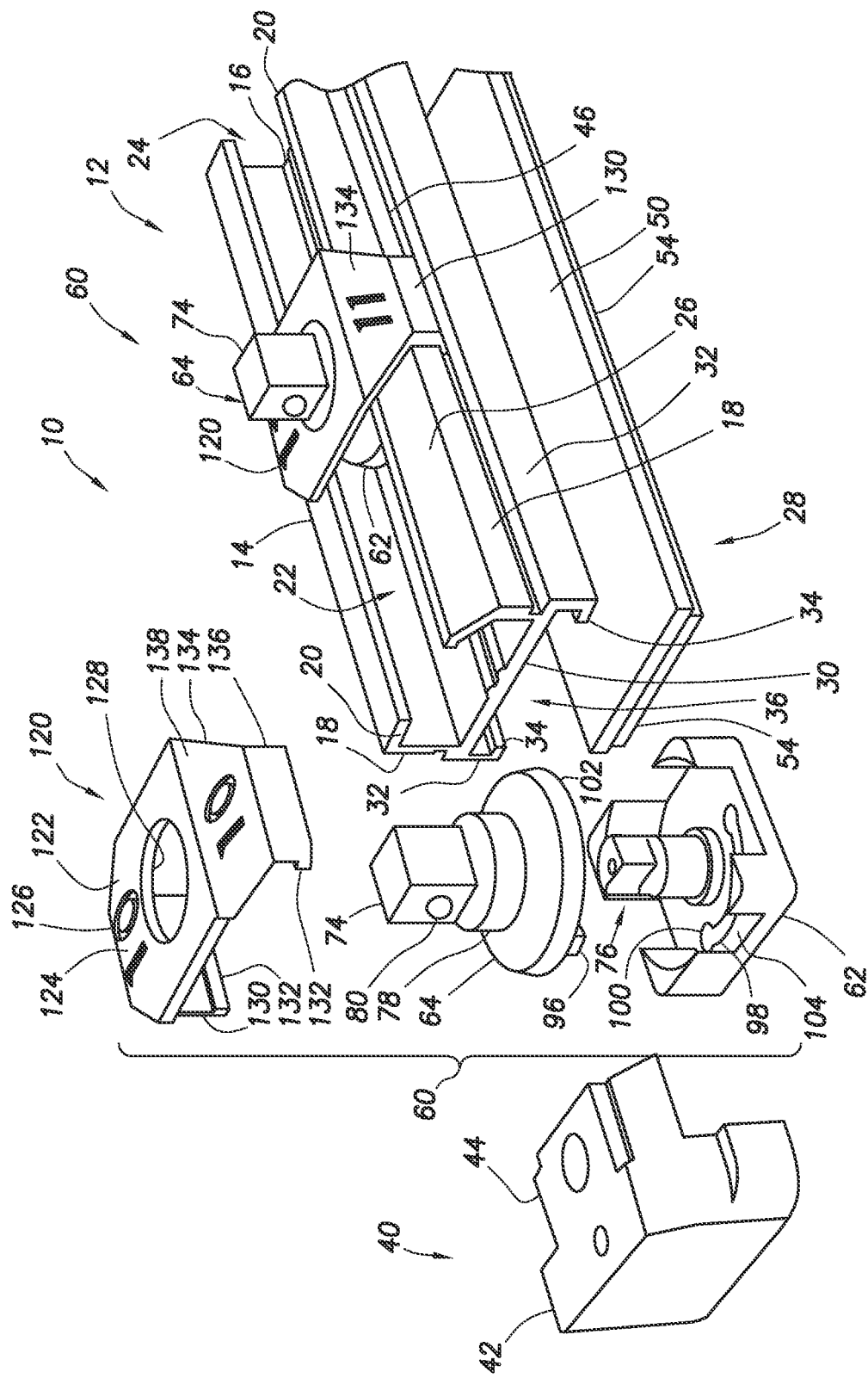
FIG. 1 is an orthogonal partially exploded view of an exemplary apparatus for releasably holding and organizing a set of sockets.
Figure 2:
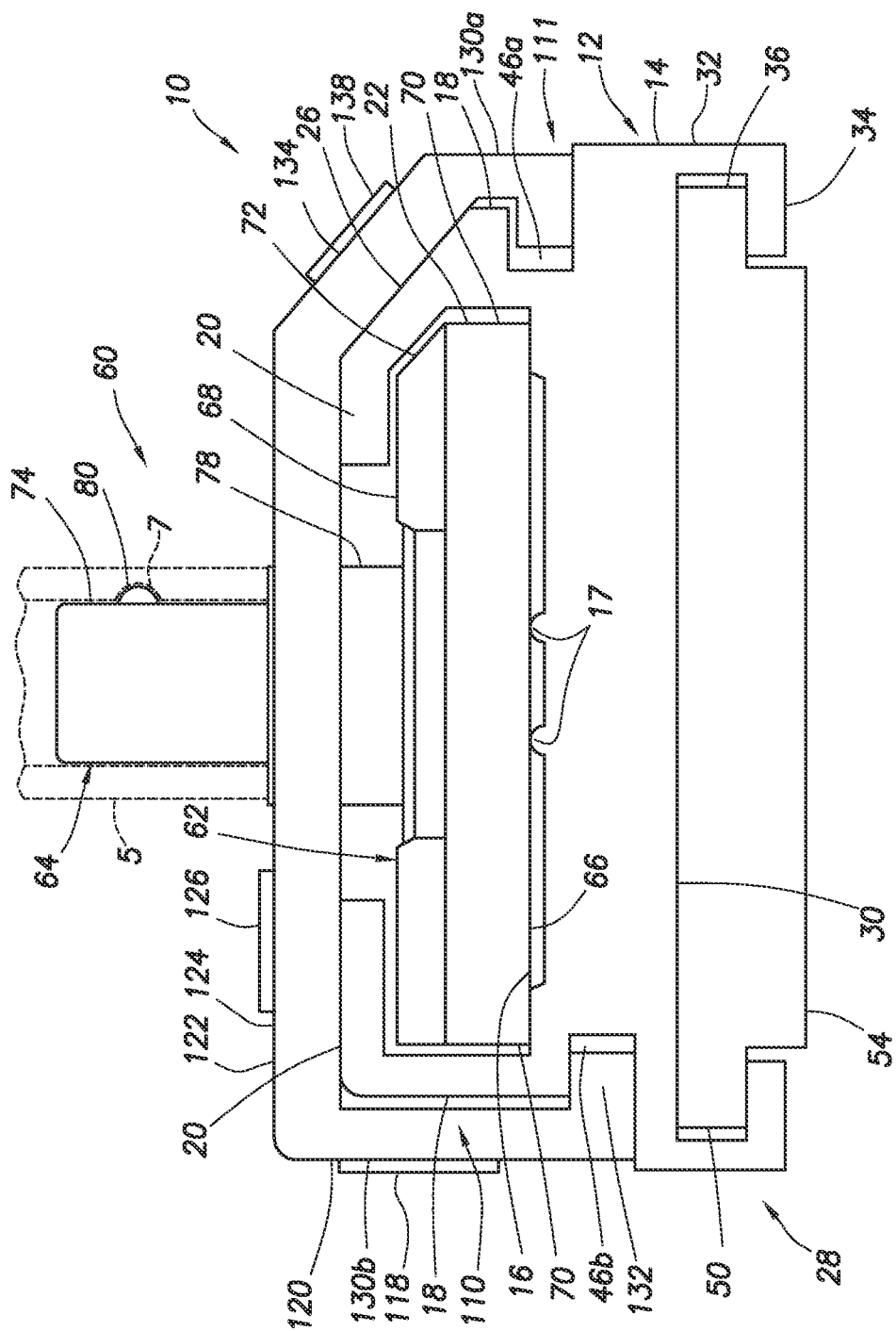
FIG. 2 is an end view of the exemplary apparatus of FIG. 1 with the end cap removed.
Figure 3:
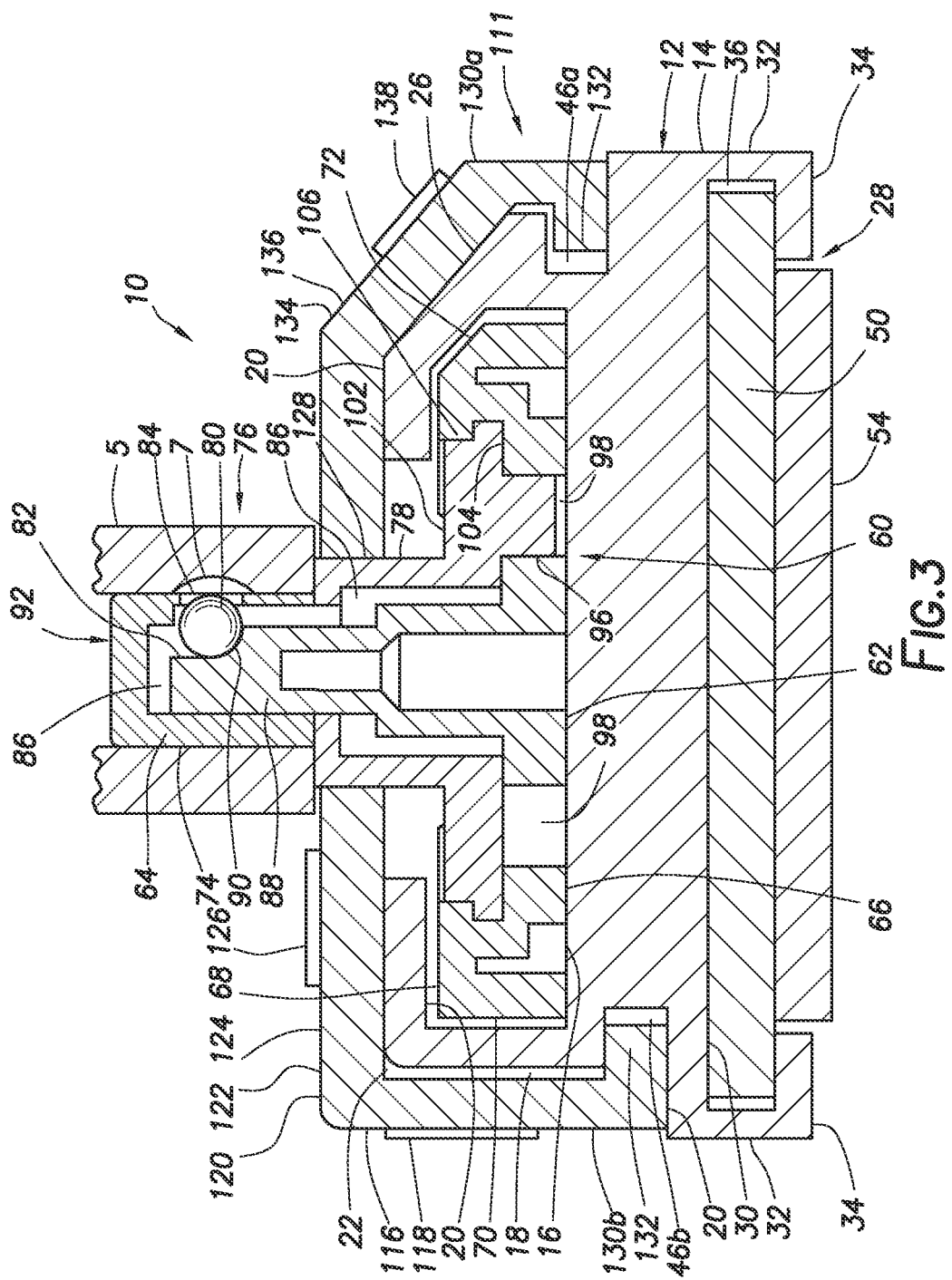
FIG. 3 is an end cross-sectional view of the exemplary apparatus of FIG. 1 taken laterally through the apparatus at a socket holder assembly.
Figure 4:
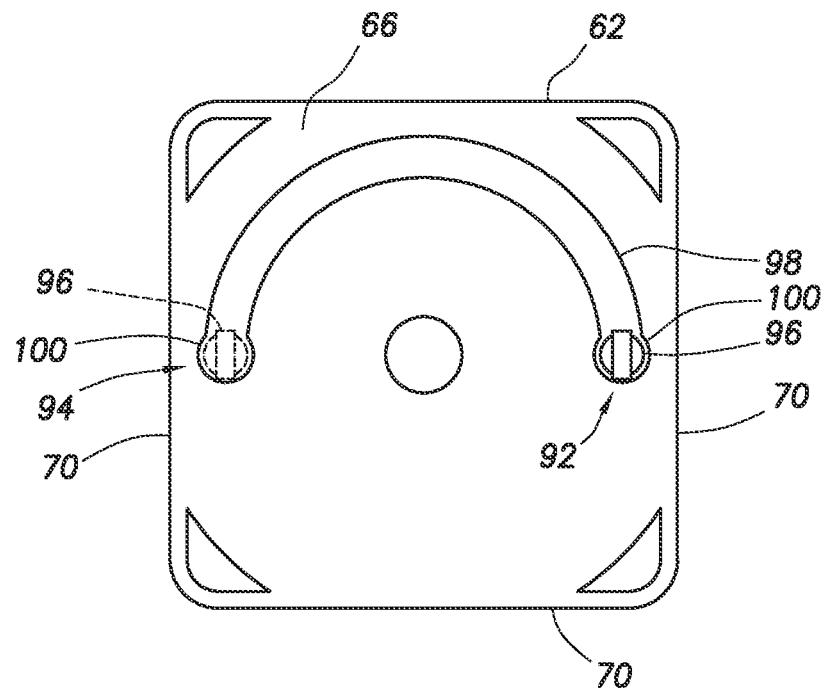
FIG. 4 is a bottom plan view of a socket holder assembly according to an aspect of the disclosure.
Figure 5:
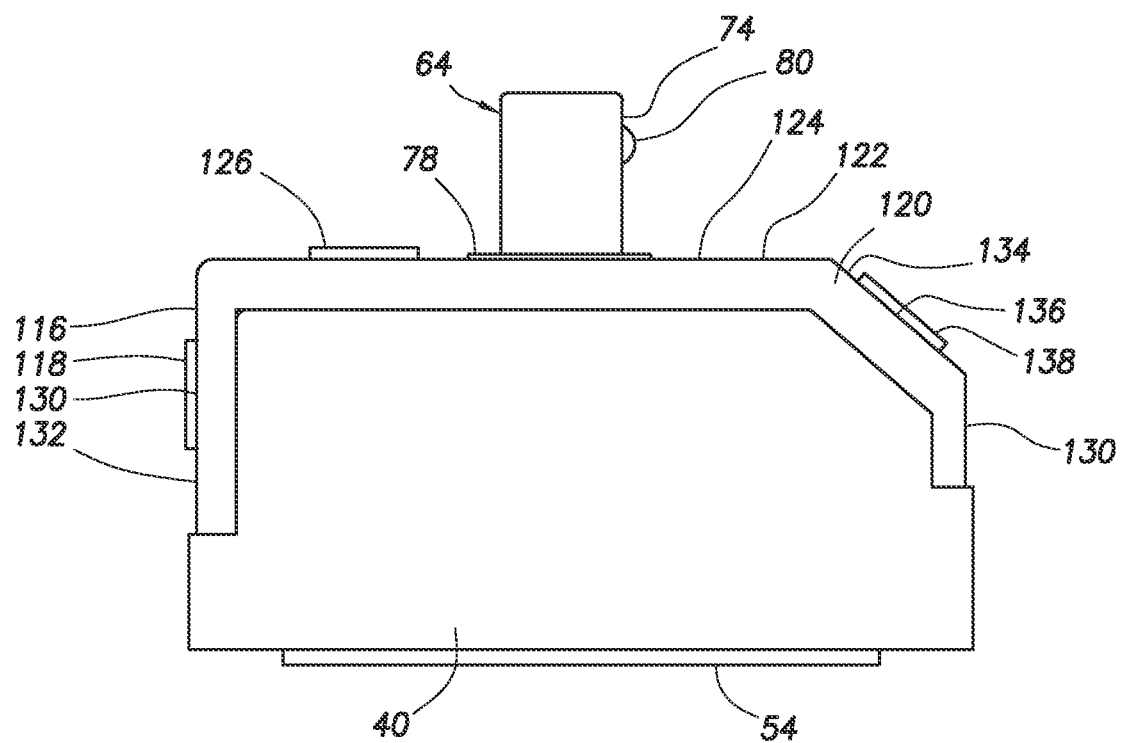
FIG. 5 is an end view of the apparatus of FIG. 1 with the end cap in place.
Figure 6:
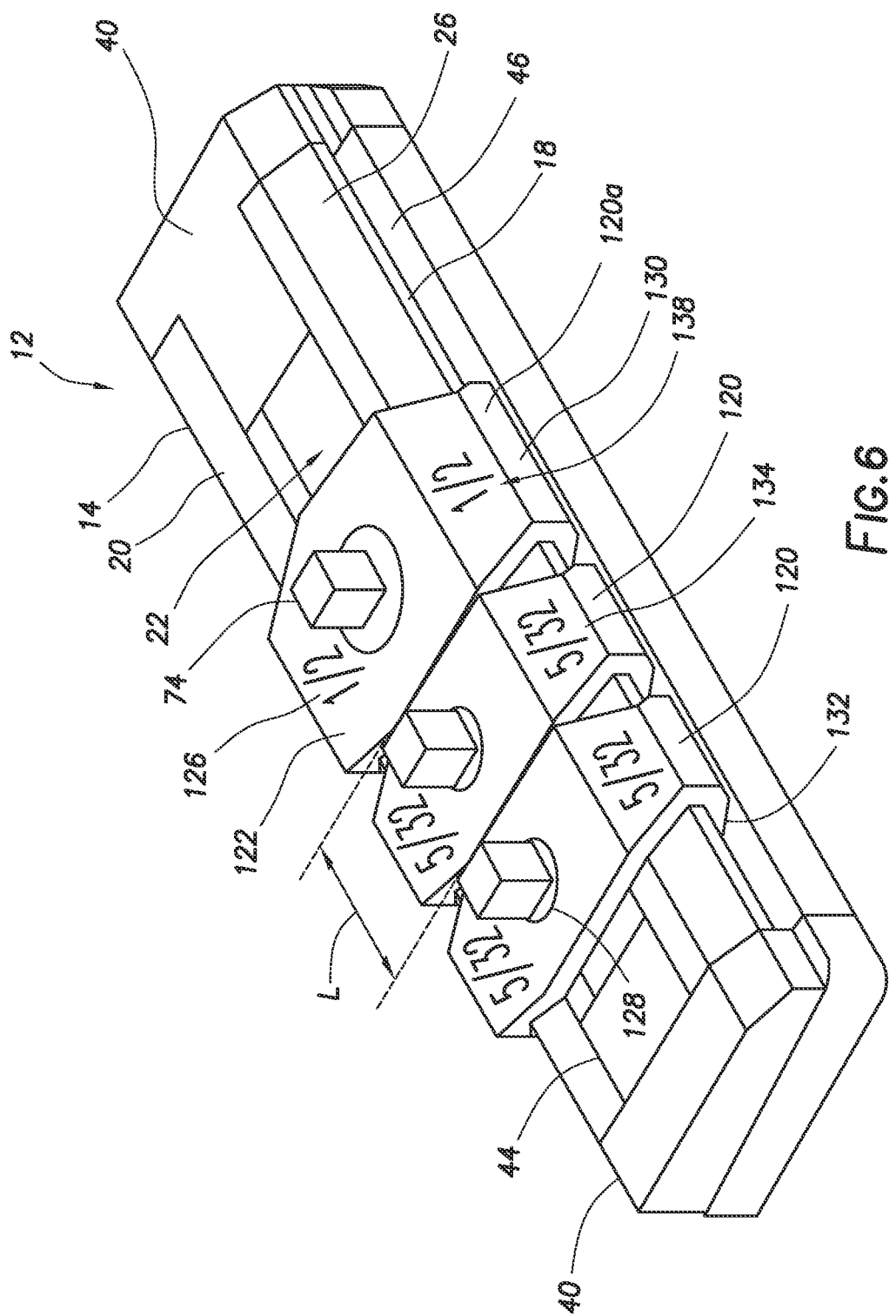
FIG. 6 is an orthogonal view of the exemplary apparatus of FIG. 1.

FIGS. 1-6 are generally discussed together to provide an understanding of the operation of the apparatus. FIG. 1 is an orthogonal partially exploded view of an exemplary apparatus for releasably holding and organizing a set of sockets. FIG. 2 is an end view of the exemplary apparatus of FIG. 1 with the end cap removed. FIG. 3 is an end cross-sectional view of the exemplary apparatus of FIG. 1 taken laterally through the apparatus at a socket holder. FIG. 4 is a bottom plan view of a socket holder assembly according to an aspect of the disclosure. FIG. 5 is an end view of the apparatus of FIG. 1 with the end cap in place. FIG. 6 is an orthogonal view of the exemplary apparatus of FIG. 1. The disclosed exemplary embodiments are specifically designed for holding sockets, however, the disclosed apparatus and methods herein enable a person of ordinary skill in the art to modify the disclosures slightly to hold other tools.

An apparatus 10 for releasably holding and organizing a plurality of tools, particularly sockets 5, is depicted. The apparatus 10 includes a rail assembly 12 having a main body 14, end caps 40, a back plate 50, and a magnetic backing plate 54. Also seen in the Figures are a plurality of socket holder assemblies 60 and a plurality of clip members 120.

The rail assembly 12 has an elongated body 14 with a cross-section characterized by a generally U-shaped channel having a bottom wall 16, opposing side walls 18, and flanges 20 which, together, define an interior channel 22. The rail assembly body 14 is shaped to cooperate with and connect to other apparatus parts, can be monolithic or of assembled parts, and can be made of various materials.

The end caps 40 include a main body 42 and a plug 44 extending therefrom and having a cross-section to slidingly engage the interior channel 22. The end cap 40 can be secured to the rail assembly body by friction fit, fasteners, such as screws, rivets, welds, bolts, and the like, adhesives, or as otherwise known in the art. Preferably the end caps are releasably attached to the body allowing selective access to one or both opposed open ends 24 of the interior channel 22. The end caps can be made of any suitable material although plastic or rubber may be preferred to provide a secure friction fit.

The back plate 50 is attached to the rail assembly body 14, by friction fit, fastener, or as otherwise known in the art. In the illustrated embodiment, the back plate 50 slidingly engages a back plate assembly 28. The back plate assembly 28 is, in the shown embodiment, defined by the rail assembly body 14 and has a generally U-shaped cross-section with a top wall 30, opposed side walls 32, and extending flanges 34 together defining an interior channel 36. The side walls and flanges engage perimeter portions of the back plate 50, holding it in position. Also shown is a magnetic plate 54 which can comprise the back plate, be attached to the rail assembly body directly or, as here, attached to the back plate 50 such as by adhesive, fasteners, etc. A magnetic plate 54 allows the assembly to be securely positioned on any suitable ferrous surface. Alternately, a non-scratch or non-skid plate, made of or coated with plastic or rubber for example, can be attached to the back plate, magnetic plate, or to the rail assembly body.

Socket Holder Assemblies

Generally seen in FIGS. 1-3 are exemplary socket holder assemblies 60. FIG. 1 shows an exploded view of a socket holder assembly 60 having a base member 62 and a mounting member 64. An assembled socket holder is also seen in FIG. 1, positioned on the rail assembly with the base member 62 engaging the interior channel 22 and the mounting member 64 extending upwardly out of the interior channel. The mounting member 64 also extends through an aperture 128 defined in the clip member 120 as addressed below.

In an exemplary embodiment of a socket holder assembly 60 seen in FIG. 2, a base member 62 engages the interior channel 22 and a mounting member 64 extends upwardly out of the interior channel 22. The base member 62 is of a size and cross-section to slidingly engage the rail assembly body 14 along the interior channel 22. The bottom wall 16 and flanges 20 of the body 14 maintain the base member 62 in the interior channel 22. The bottom wall 16 may include friction (or anti-friction) features 17 to reduce (or increase) the force required to slide the socket holder assemblies along the rail assembly. For example, such features may include longitudinally extending ridges, a high-friction or low-friction longitudinal insert, layer, or coating, etc., as is known in the art. The features 17 can be of metal, plastic, rubber or other material and can be of a piece with the bottom wall or mounted thereon.

The mounting member 64 of the socket holder assembly 60 defines a mounting post 74, a detent assembly 76, and a columnar shoulder 78 in the embodiments at FIGS. 1-6. The mounting post 74 is generally square to accept the drive end of a typical socket. The mounting member 64 includes a detent assembly 76 for interacting with a corresponding detent 7 defined in the interior wall of the socket 5. A typical detent assembly 76 includes a detent ball 80 and a biasing mechanism 82 for permanently or selectively biasing the detent ball radially outward and into engagement with the corresponding detent defined in the socket. Biasing mechanisms 82 are known in the art and can include a coil spring mounted in an interior space of the mounting post 74, a leaf spring defined by or mounted on the mounting post 74, or an elastic and resilient detent "ball" defined by or mounted on the exterior of the mounting post 74. Alternately, the biasing mechanism can be actuated by a user, such as by causing relative movement of socket holder assembly pieces.

In the embodiment shown, and as best seen in FIG. 3, the detent assembly 76 is rotatably actuated by a user. The base member 62 and the mounting member 64 are rotatably attached. In the embodiment shown, the mounting member 64 includes a rotary disk 102 which rotatingly engages a corresponding support surface 104 defined on the base member 62. The rotary disk 102 can be held in engagement with the base member 62 by flanges 106 defined on the base member 62, for example.

The mounting member 64 defines an interior space 86 extending into the mounting post 74. The mounting post 74 defines a detent ball aperture 84 of smaller diameter than the detent ball 80 such that the ball 80 can extend partially through the aperture but cannot exit the interior space entirely. The detent ball 80 is trapped in the interior space 86 between the mounting post 74 and a locking pin 88 defined on the base member 62 and which extends through the interior space 86.

The upper end of the locking pin 88 defines a cam surface 90 which engages and moves the detent ball 80 radially between an unlocked position 92, seen in FIG. 3 for example, in which a socket is held in place by the detent ball, and a locked position 94, seen in FIG. 2 for example, in which the socket is released from the socket holder.

In use, a socket drive end is placed over the mounting post 74 and the socket and mounting member 64 are rotated with respect to the base member 62 and locking pin 88. In the unlocked position, the detent ball is positioned radially inwardly, as in FIG. 3, and does not engage the detent 7 defined in the interior surface of the socket 5. In the locked position 94, as seen in FIG. 2, the detent ball 80 is forced radially outward and partially through the aperture 84 by relative motion of the cam surface 90 and into locking engagement with the detent 7 of the socket 5.

As seen in FIGS. 1 and 3-4, the socket holder assembly 60 can further include one or more locking tabs 96 extending downwardly from the mounting member 64. The locking tab 96 extends through and slidingly engages a cooperating arcuate slot 98 defined in the base member 62. Recesses 100 can also be defined at the ends of the arcuate slot 98 to hold the socket holder assembly in the selected locked or unlocked position until the user actuates the assembly and to provide the user a tactile response indicating achievement of a selected position as the tab snaps into the recess. In the embodiment shown, rotation of the mounting member 64 (and locking pin 88 and tab 96) by a one-half turn moves the detent assembly between the locked position 94 and unlocked position 92 and the locking tab 96 between opposing ends of the arcuate slot 98.

The socket holder assemblies 60 can be of various design without departing from the spirit of the disclosure as will be understood by those of skill in the art. In some embodiments, the base member and mounting member are monolithic, such as where a resilient or cantilevered detent "ball" is defined on the mounting post 74 of the mounting member 64. In other embodiments, the base 62 and mounting members 64 are fixedly attached or not relatively movable, such as where the detent assembly is of the "push-on" variety and comprises a spring-biased detent ball. In yet other embodiments, the base 62 and mounting members 64 are rotatably attached, such as where the detent assembly is actuated by rotation of the mounting post 74 with respect to the locking pin 88, as seen herein, for example.

Clip Members

Exemplary clip members 120 cooperate with the rail assembly 12 and a socket holder assembly 60. In the embodiment shown in FIGS. 1-6, the clip member 120 comprises a central plate 122 defining a generally planar upper surface 124 with socket identification indicia 126 thereon. An aperture 128 is defined through the central plate 122 for cooperation with the mounting member 64, and more specifically the columnar shoulder 78 which fits closely through the aperture 128. In an embodiment, the columnar shoulder upper surface is flush with the upper surface 124 of the central plate 122.

Each clip member 120 slidingly and grippingly engages grooves 46 defined in the side walls 18 of the rail assembly body 14. The clip member 120 has a central plate 122, opposing legs 130, and flanges 132. The central plate 122, in the illustrated embodiment, rests on the rail assembly flanges 20. The grooves 46 are grippingly engaged by the flanges 132 and the clip member is maintained on the rail assembly. In an embodiment, the legs 130 of the clip members are flexible and the clip member is "snapped" into an engaged position by pressing the clip member downward onto the rail assembly, flexing the legs 130 outwardly until the clip member 120 snaps around the body 14.

Alternately, the clip members 120 can be slidingly engaged onto and removed from the rail assembly body 14 at the ends of the rail assembly 12, either over an open end 24 of the interior channel 22 or over an end cap 40. In an embodiment, at least one end cap 40 defines a cross-section which cooperates with the clip member 120, allowing the clip member 120 to readily slide over the end cap 40 and onto the rail assembly side walls 18 at grooves 46. The end cap 40 can optionally define grooves (not shown) aligned with grooves 46. In another embodiment, at least one end cap 40 is removable from the rail assembly body 14, such as by pulling the end cap 40 to overcome a friction fit between the end cap plug 44 and the channel walls 18, allowing the clip member 120 to be slid over an open end 24 of the channel 22 and onto the rail assembly body 14.

In an embodiment, the clip members are constrained against rotational movement in relation to the rail assembly. The clip member is constrained against rotational movement in relation to the rail assembly by interference between opposing legs of the clip member and at least a side wall of the rail assembly.

In some embodiments, as seen, the clip member 120 further includes an angled plate 134 corresponding to the angled wall 26 of the rail assembly body 14. The angled plate 134 extends from the central plate 122 at a relative angle of between 10 and 80 degrees and defines an angled surface 136 for indicia 138.

In use, the rail assembly is often transferred from one surface and orientation to another depending on the job. The assembly can be selectively mounted by the magnetic backing, for example, on a horizontal, vertical or other surface, and above, at, or below eye level. Regardless of mounting orientation or height relative to the user, the indicia 138 on the angled surface 136, indicia 126 on the central plate 122, and/or indicia 118 on a vertical surface 116 of a leg 130 should be visible to the user.

The indicia provides socket identification information, for example, socket size in metric or standard units, and/or socket type, and/or indications for locking and unlocking the socket from the socket holder. The indicia 118, 126, and 138 on any given clip member can be identical or different.

Further, as with the base member 62 and channel 22, the cooperating angled plate 134 and angled wall 26 of the rail body 14 can act as an orientation guide for orientation of the clip member on the rail assembly. In another embodiment, an angled plate can be provided on both lateral sides of the clip member.

Figure 11:
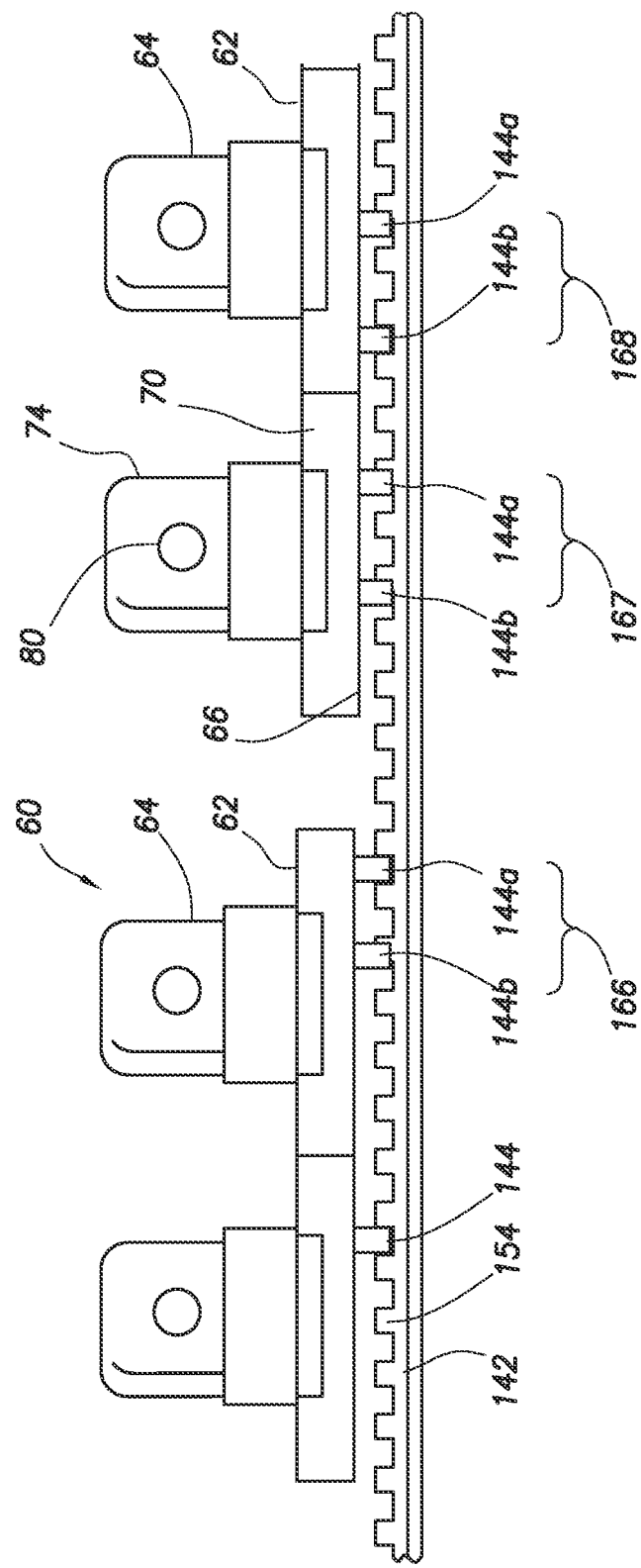
FIG. 11 is an orthogonal and exploded view of a positioning assembly and socket holder assemblies of the exemplary apparatus of FIG. 7.

Adjacent clip members 120 or adjacent socket holder assemblies 60 can, as seen in FIGS. 9 and 11, abut one another defining a minimum spacing between adjacent, mounted sockets of the same or similar diameter. Socket sets typically have multiple sockets of small diameter and the clip members 120 each have a length, L, of greater than the socket diameter to maintain spacing between adjacent mounted sockets. However, many socket sets include multiple sockets of relatively larger diameters due to the larger size of fastener for which the sockets are employed. Where larger diameter sockets are mounted on adjacent socket holder assemblies, the disclosure provides a mechanism to maintain sufficient spacing to prevent the larger sockets from knocking together during transport and reorientation of the rail assembly.

In FIG. 6, each clip member 120 has a longitudinal length, L, of greater than the diameter of the socket for which it is used. Various smaller diameter sockets can be placed on a clip member having a typical length. In an embodiment, a typical clip member 120 has a length, L, equal to the length of a side 70 of its corresponding base member 62, as seen in FIGS. 1 and 9. However, some larger sockets will have diameters exceeding the length of a socket holder base member 62. In such a case, a clip member 120*a* has a length greater than the diameter of the larger socket and greater than the length of its corresponding base member 62. The larger clip member 120*a* abuts adjacent clip members 120 and maintains a minimum spacing on either side of the larger diameter socket.

As an example, a typical small socket base diameter is $^{15}\!/_{32}$ inches (approximately one-half inch), which size may be used for a number of sockets for differently sized fasteners. For such sockets, the clip members 120 can have a length of approximately three-quarters inches. A larger diameter socket may have a diameter of one and one-half inches or greater. As an example, a two and one-half inch diameter socket can use a three inch long clip member. For such sockets, clip members 120 are provided having lengths greater than the diameter of the designated socket.

Orientation Guides

As seen in FIGS. 2-3, the rail assembly further includes an exemplary orientation guide 110 for orienting the socket holder assemblies 60 in the interior channel 22. The orientation guide 110 requires a base member 62, and therefore socket holder assembly 60, to be inserted into the interior channel 22 at specified orientations. Thus, a set of socket holder assemblies would necessarily "face the same way" in the channel. One possible orientation guide is shown.

The base member defines a bottom surface 66, a top surface 68, and four side surfaces 70 which together define a base member 62 having a shape generally similar to that defined by the bottom wall 16, side walls 18, and flanges 20 of the channel 22. The rail assembly body 14 further defines an angled wall 26 between one of the flanges 20 and a side wall 18. The angled wall 26 is oriented at an angle between 10 and 80 degrees with respect to both the adjacent flange 20 and side wall 18. Similarly, the base member 62 defines a corresponding beveled surface 72. On the opposite side of the channel 22, the opposed flange 20 and side wall 18 define a different angle of intersection, such as the right-angled intersection shown. The base member 62 then defines a corresponding right-angled intersection at the adjacent side 70 and top 68. The corresponding shapes provide an orientation guide wherein the socket holder assemblies cannot be inserted into the channel except at coordinating orientations.

Stated another way, the channel of the rail assembly comprises an orientation mechanism which cooperates with a corresponding alignment feature defined on each socket holder, the alignment mechanism preventing insertion of the socket holder into the channel of the rail assembly unless the alignment feature and the alignment mechanism are cooperatively aligned. The alignment mechanism comprises a shaped surface on a wall of the rail assembly and the aligning feature comprises a cooperating shaped surface on the base.

FIGS. 1-3 and 5 present another embodiment of an orientation guide 111 employing the clip members 120 and the rail assembly 12. Features may best be seen at FIGS. 2-3. The clip member 120 has opposing legs 130 positioned on opposing sides of the rail assembly body 14. However, the end of leg 130a is at a lower height than the end of the leg 130b. Where the clip member 120 employs two mirror image legs 130 (e.g., having no angled plate 134), one leg 130a is longer than the other leg 130b. Where the clip member has a single angled plate 134, as shown, the leg 130b is longer vertically than the vertical extent of the angled plate 134 and leg 130a combined. Corresponding to the differing heights of the ends of the legs 130a-b, the grooves 46a-b on the side walls 18 of the body 14 are at differing and corresponding heights. Such an arrangement requires a selected orientation of a clip member 120 to engage the grooves 46. A set of clip members will all then "face the same direction." The orientation guides can be used alone, in combination, or not at all in various embodiments.

Stated another way, the rail assembly body comprises an orientation mechanism which cooperates with a corresponding alignment feature defined on each clip member, the alignment mechanism preventing attachment of the clip member onto the rail assembly unless the alignment feature and the alignment mechanism are cooperatively aligned. The alignment mechanism comprises two grooves, one groove defined along each side wall of the channel, the two grooves at different relative heights (e.g., different heights above the bottom wall of the channel), and the aligning feature comprises two opposed legs of a clip member, each leg having an end extending to engage one of the two grooves. The flanges of the clip members at the ends of the legs engage the grooves.

Rail System with Socket Holder Positioning Mechanism

Figure 7:
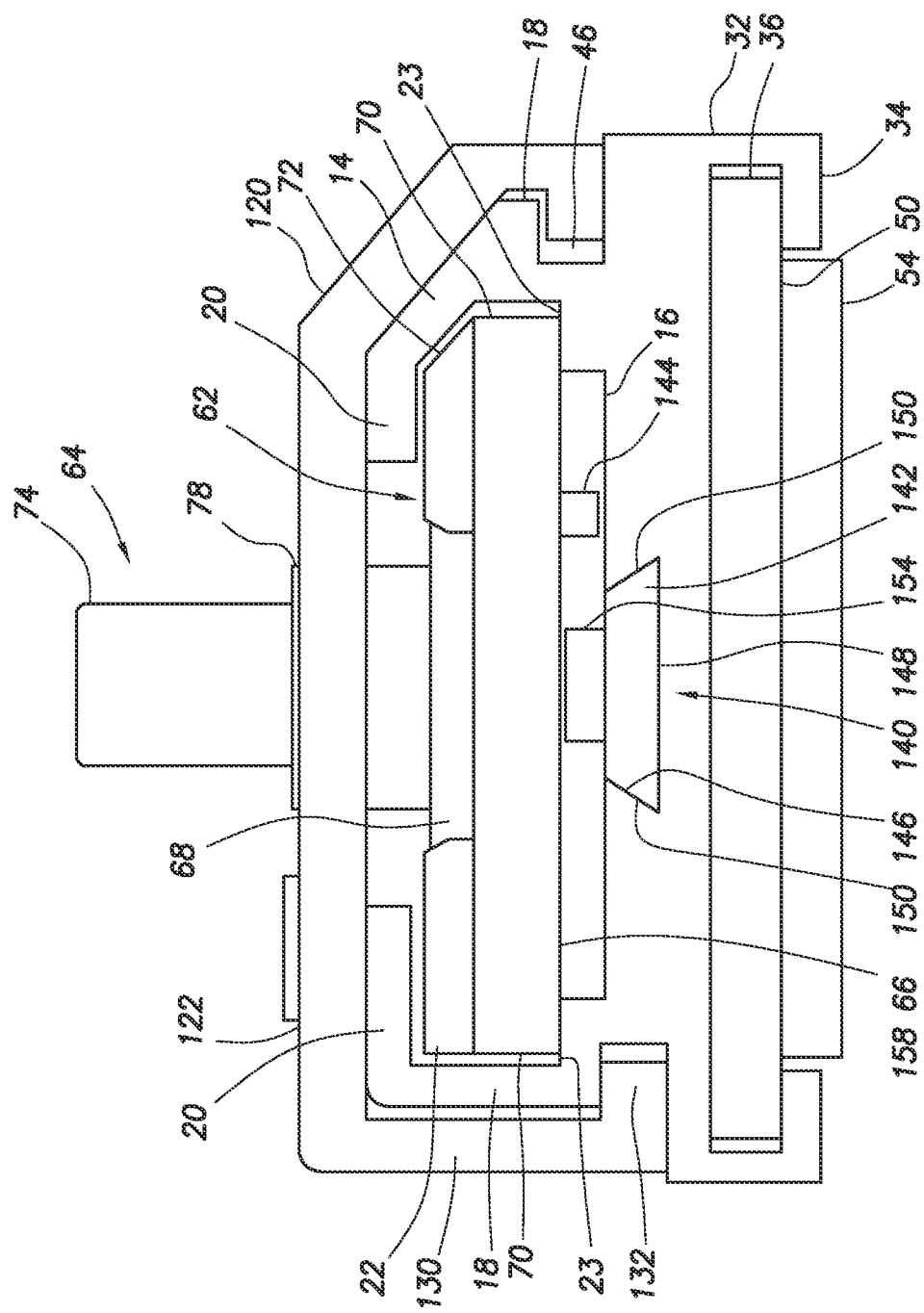
FIG. 7 is an end view, with the end cap removed, of an exemplary apparatus according to an aspect of the disclosure having a positioning mechanism for socket holder assemblies.
Figure 8:
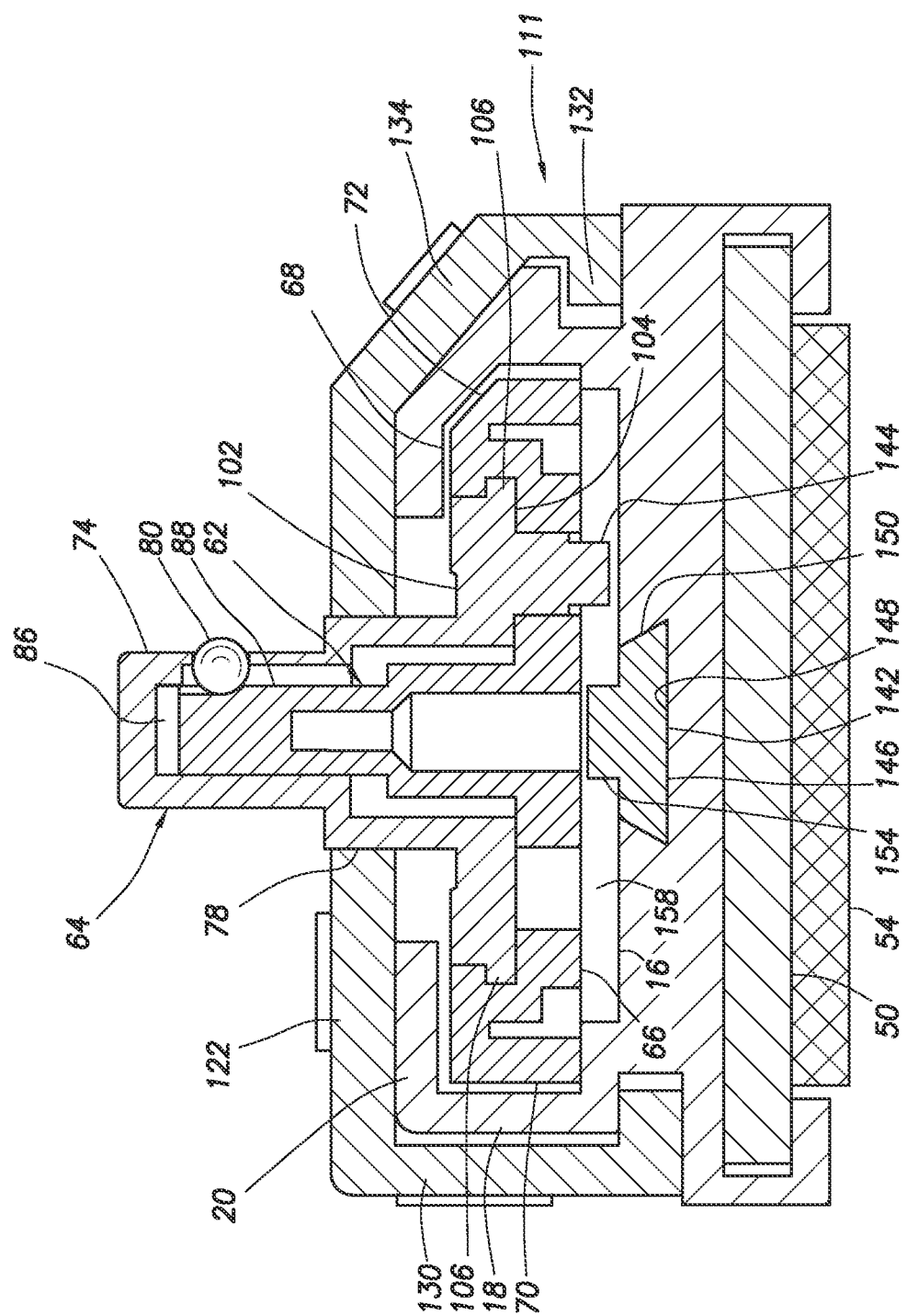
FIG. 8 is an end cross-sectional view of the exemplary apparatus of FIG. 7 taken laterally through the apparatus at a socket holder assembly.

FIGS. 7-11 are generally discussed together to provide an understanding of the operation of the apparatus. Many of the specific features and functions of the exemplary apparatus of FIGS. 8-12 are identical or similar to those found in the exemplary embodiment discussed at FIGS. 1-8. Consequently, the following discussion is limited to distinctions and differences, with like part numbers used for like or similar parts. FIG. 7 is an end view, with the end cap removed, of an exemplary apparatus according to an aspect of the disclosure having a positioning mechanism for socket holder assemblies. FIG. 8 is an end cross-sectional view of the exemplary apparatus of FIG. 7 taken laterally through the apparatus at a socket holder. FIG. 9 is a longitudinal cross-sectional view of the exemplary apparatus of FIG. 7. FIGS. 10A-D are bottom plan views of various embodiments of socket holder assemblies for use in the apparatus of FIG. 7. FIG. 11 is an orthogonal and exploded view of a positioning assembly and socket holder assemblies of the exemplary apparatus of FIG. 7.

Seen in FIG. 7 is a socket holder positioning mechanism 140 including a positioning member 142 along the channel and cooperating tabs 144 defined on the socket holder assembly 60. The rail assembly has elongated body 14 characterized by a channel having a bottom wall 16, opposing side walls 18, and flanges 20 which define an interior channel 22. The interior channel 22 further defines a pair of longitudinally extending and opposed shoulders 23. The longitudinal shoulders 23 engage the bottom 66 of the socket holder assembly base member 62 and support the socket holder assembly 60 spaced above the bottom wall 16. Thus a longitudinal space 158 is defined between the bottom surfaces 66 of the socket holder assemblies 60 and the bottom wall 16 of the channel 22.

Further defined by the body 14 and positioned extending longitudinally along the bottom wall 16, is a socket holder positioning member 142. In the embodiment shown, the positioning member 142 is a longitudinal strip 152 which slidingly engages a sub-channel 146 having a bottom wall 148 and opposed side walls 150. The side walls 150 are angled toward one another to maintain the positioning member 142 in place in the sub-channel 146 in the embodiment shown. The sub-channel can take other cross-sectional shapes, having orthogonal side walls, flanges for engaging a positioning member, etc. Further, the positioning member 142 can be adhered, fastened or otherwise attached to the rail assembly, along a sub-channel 146, the interior channel 22, or another surface suitable to the purpose. The positioning member 142 can be of metal, plastic, rubber or other material. Further, the positioning member 142 can be comprised of alternating ridges and slots defined by or mounted on the bottom wall 16 of the body 14.

The positioning member 142 in the embodiment shown comprises a longitudinal strip 152 and a plurality of laterally extending, longitudinally spaced-apart ridges 154, as best seen at FIGS. 9 and 11. The ridges 154 extend vertically above the bottom wall 16 of the interior channel 22 and into the interior channel 22 and into the space 158. The ridges may take various shape.

In FIGS. 7-12, each socket holder assembly 60 defines at least one cooperating positioning tab 144 extending below the bottom surface 66 of the base member 62 of the assembly. The positioning tabs 144 selectively engage the ridges 154. The positioning tabs 144 are defined on the mounting member 64 of the socket holder assembly 60 and extend through one or more cooperating arcuate slots 156 defined through the base member 62. Rotation of the mounting member 64 with respect to the base member 62 results in movement of the positioning tabs 144 along the slot 156.

Figure 10A:
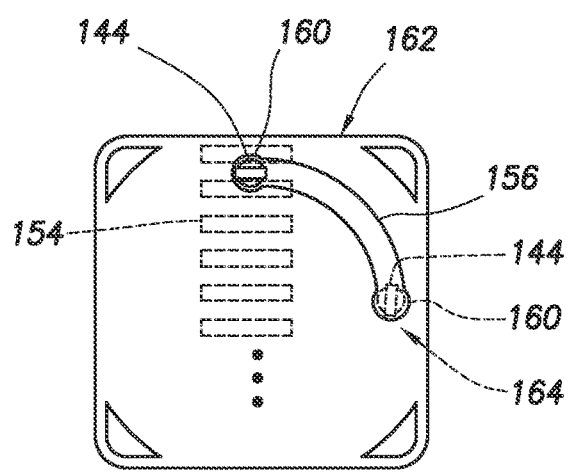
FIGS. 10A-D are bottom plan views of various embodiments of socket holder assemblies for use in the apparatus of FIG. 7.

In an embodiment, seen at FIGS. 8 and 10A, a single positioning tab 144 extends from the mounting member 64 through a cooperating arcuate slot 156 in the base member 62 and into the longitudinal space 158 defined between the bottom 66 of the base member 62 and the bottom wall 16 of the interior channel 22. The positioning tab 144 vertically overlaps with the ridges 154 as both extend, from opposite sides, into the space 158.

The mounting member 64 and positioning tab 144 rotate between an engaged position 162, wherein engagement of a positioning tab 144 and a ridge 154 prevents longitudinal movement of the socket holder 60 along the rail assembly, and an unengaged position 164, wherein the socket holder 60 is free to slide longitudinally along the rail assembly. FIGS. 10A and 11 show a positioning tab 144 in an engaged position 162 between adjacent ridges 154 in solid lines. Attempted sliding movement of the socket holder assembly 60 is prevented by contact between the positioning tab 144 and a ridge 154. FIGS. 7-8 and 10A, in dashed lines, show a positioning tab 144 in an unengaged position 164.

FIGS. 10A-D are bottom plan views of exemplary base members for a socket holder assembly according to various aspects of the disclosure showing other arrangements for locking and positioning tabs.

FIG. 10A shows a positioning tab 144 in an engaged position 162 (solid lines) and in the unengaged position 164 (dashed lines). The relative location of selected ridges 154 (dashed lines) are provided to indicate cooperation between the tab and ridge elements of the positioning mechanism. The tab 144 extends through the arcuate slot 156 which can define recesses 160 for holding the positioning tab 144 in a selected position until moved by the user. In one embodiment, the positioning tab 144 is rotated between engaged and unengaged positions by one-quarter turn of the mounting member 64.

In the embodiment at FIG. 10A, the positioning tab 144 can also serve as a locking tab 96. That is, the positioning tab 144 is moved from an unengaged position to an engaged position with respect to the ridges 154 while simultaneously the mounting member 64 is moved from a locked position 94, wherein the detent ball 80 is moved radially outward and holds a socket on the mounting post 74, to an unlocked position 92, wherein the detent ball 80 is radially released inward.

Figure 10B:
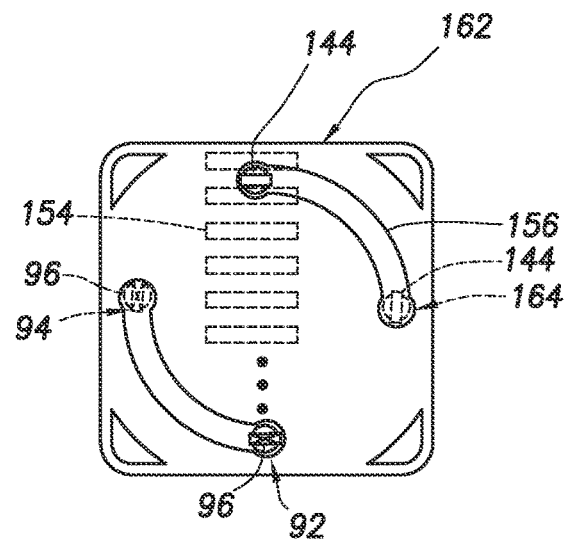

Alternatively, and as seen in FIG. 10B, the locking tab 96 moves between locked 94 and unlocked 92 positions as a positioning tab 144 moves between engaged 162 and unengaged 164 positions. Hence, the socket holder assembly is free to slide along the rail assembly when it is not holding a socket and is securely positioned on the rail assembly when the mounting member is in the locked position (whether a socket is locked to the mounting post 74 or the mounting post 74 is not engaged by a socket). In the embodiment shown, a quarter-turn of the mounting member moves the socket holder assembly between locked and unlocked positions and between engaged and unengaged positions.

Figure 10C:
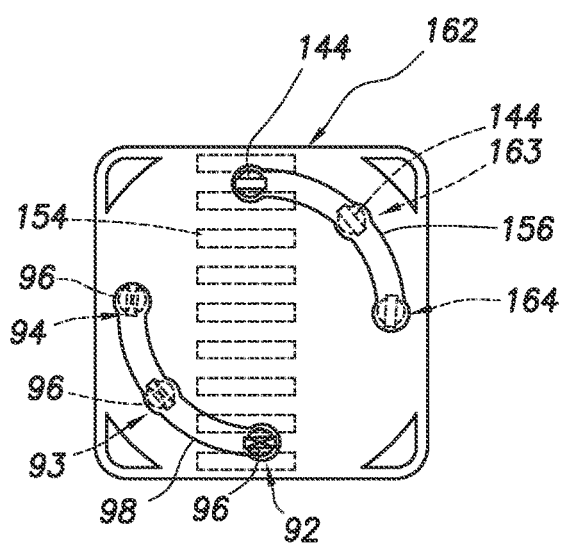

As another alternative, in FIG. 10C the locking tab 96 and the positioning tab 144 each move between three corresponding positions. The locking tab 96 rotates from a locked position 94, to an intermediate and locked position 93, to an unlocked position 92. Simultaneously and due to the same rotation of the mounting member 64, the positioning tab 144 moves from an engaged position 162, to an intermediate and unengaged position 163, to an unengaged position 164. Hence the socket holder assembly 60 can be held in a selected position on the rail assembly by engagement of the positioning tab 144 with the ridges 154 in the engaged position 162 while the socket holder assembly 60 is in the locked position 94 (with or without a socket engaging the mounting post 74).

Rotation of the mounting member 64 to place the locking tab 96 in the intermediate and locked position 93 also places the positioning tab 144 in the corresponding intermediate and unengaged position 163, allowing sliding movement of the socket holder assembly 60 along the rail assembly while a socket is locked on the mounting post 74. Further rotation in the same direction of the mounting member 64 moves the locking tab 96 to the unlocked position 92 and simultaneous movement of the positioning tab 144 to the unengaged position 164, allowing sliding movement of the socket holder assembly with the socket holder assembly in the unlocked position. In an embodiment, rotation between adjacent positions requires a one-eighth turn of the mounting member with respect to the base member 62, while rotation between the extreme positions requires a one-quarter turn. Stated another way, a one-eighth turn moves the socket holder assembly between engaged and unengaged positions, while a one-quarter turn locks or unlocks a socket.

In an exemplary multi-tab arrangement having a pair of positioning tabs 144 per socket holder assembly, two positioning tabs 144 extend from the mounting member 64 through a cooperating slot 156 in the base member 62 and into the longitudinal space 158 defined between the base member 62 and the bottom wall 16 of the interior channel 22.

Figure 10D:
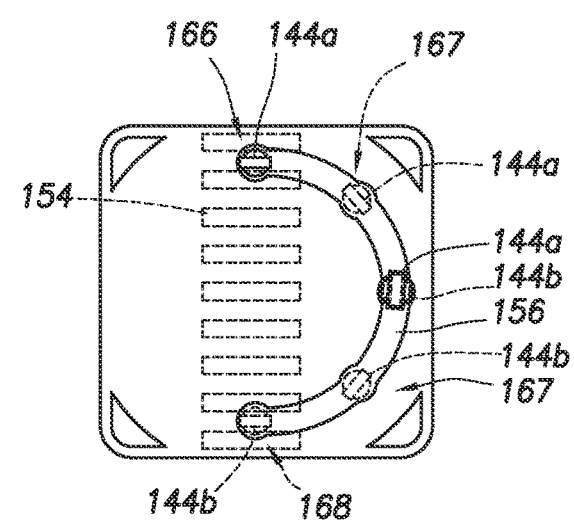

FIGS. 9, 10D, and 11 best show a pair of positioning tabs 144a-b which rotate between three positions. A first engaged position 166 is defined wherein one of the pair of tabs, tab 144a, engages at least one ridge 154 of the positioning member 142 thereby preventing sliding of the socket holder assembly. The tabs 144a-b are rotatable to an unengaged position 167 wherein the socket holder assembly 60 is free to slide along the rail assembly (not seen in FIG. 9). The tabs 144 are further rotatable into a second engaged position 168, wherein the other of the pair of positioning tabs, tab 144b, engages at least one ridge 154 of the positioning member 142 thereby preventing sliding of the socket holder. In an embodiment, rotational movement from the first engaged position to the second engaged position corresponds to one-quarter turn of the mounting member 64 while movement from either the first or second engaged positions to the unengaged position corresponds to a one-eighth turn of the mounting member.

As with the other embodiments, the positioning tabs 144 extend through and cooperate slidingly with an arcuate slot 156 and extend further into the space 158 defined between the base member 62 and the bottom wall 16 of the interior channel 20.

In an alternative embodiment and still with reference to FIG. 10D, a positioning tab 144 can also serve as a locking tab 96 such that rotation of the tabs 144a-b perform both functions of moving the socket holder assembly between unlocked and locked positions and moving the assembly between engaged and unengaged positions.

Figure 14A:
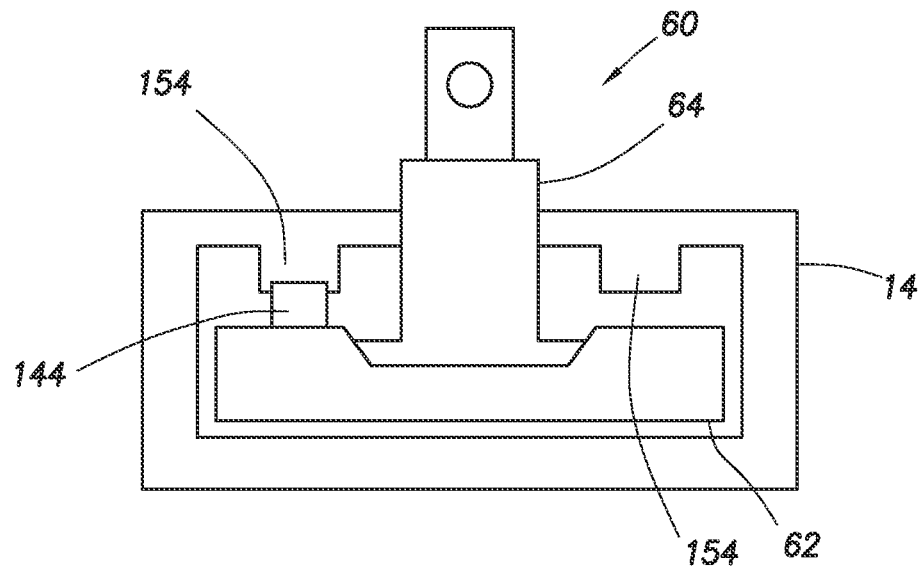
FIGS. 14A-B are elevational plan views of alternate embodiments of socket holder assemblies and rail assemblies according to aspects of the invention.
Figure 14B:
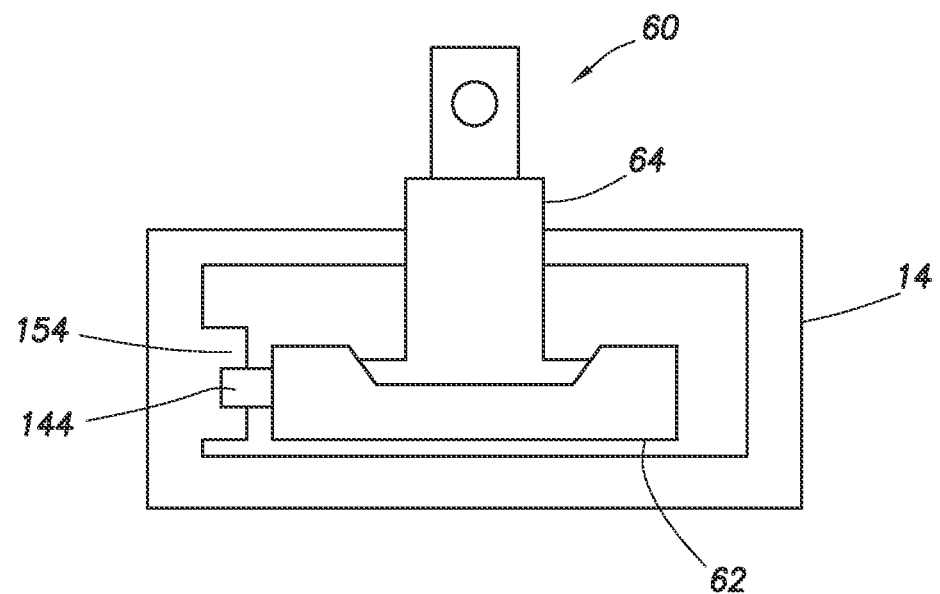

Turning briefly to FIGS. 14A-B, alternate embodiments of positioning assemblies 140 are seen according aspects of the disclosure. In FIG. 14A, the positioning tab 144 is defined on the mounting member 64 at the rotary disk 102 and extends upwardly to vertically overlap and cooperate with ridges 154 defined on the interior of the channel 22 at the rail assembly flanges 20. Rotation of the mounting member 64 moves the tab 144 into or out of engagement with the ridges 154. A single positioning tab 144 can move between engaged positions on either side of the rail assembly channel 22, cooperating with ridges 154 defined on either side, as shown. In such embodiment, the socket holder assembly 60 can be placed in a disengaged position by an eighth or a quarter turn of the mounting member 64 and moved between two engaged positions by a one-half turn of the mounting member. Alternately, two positioning tabs 144 can be defined on the mounting member 64, positioned 90 degrees apart, such that the socket holder assembly 60 is held in position at two engaged positions, one quarter turn apart. Further, two opposed positioning tabs 144 can be defined on the mounting member 64, positioned 180 degrees apart, such that the socket holder assembly 60 is held simultaneously by tabs on both side of the rail assembly. The upwardly extending tabs 144 can be defined on the rotary disk 102 as shown or on another surface of the mounting member 64.

FIG. 14B shows an alternate arrangement wherein the Positioning tabs 144 are defined extending radially from the mounting member 64 to engage with cooperating ridges 154 defined along the side walls 18 of the rail assembly 12. Similarly to the arrangements described above, the exemplary radial tab 144 can move between engaged and disengaged positions. Multiple radial tabs can be used, spaced apart by 90 degrees or opposed to one another, to provide alternate fractional turns of the mounting member 64 and engagement on both side walls simultaneously. Radial tabs can be defined on the rotary disk 102, the shoulder 78 or other appropriate surface of the mounting member 64. Other arrangements will be apparent to those skilled in the art.

Socket Holders with Mounted Clip Members

Figure 12:
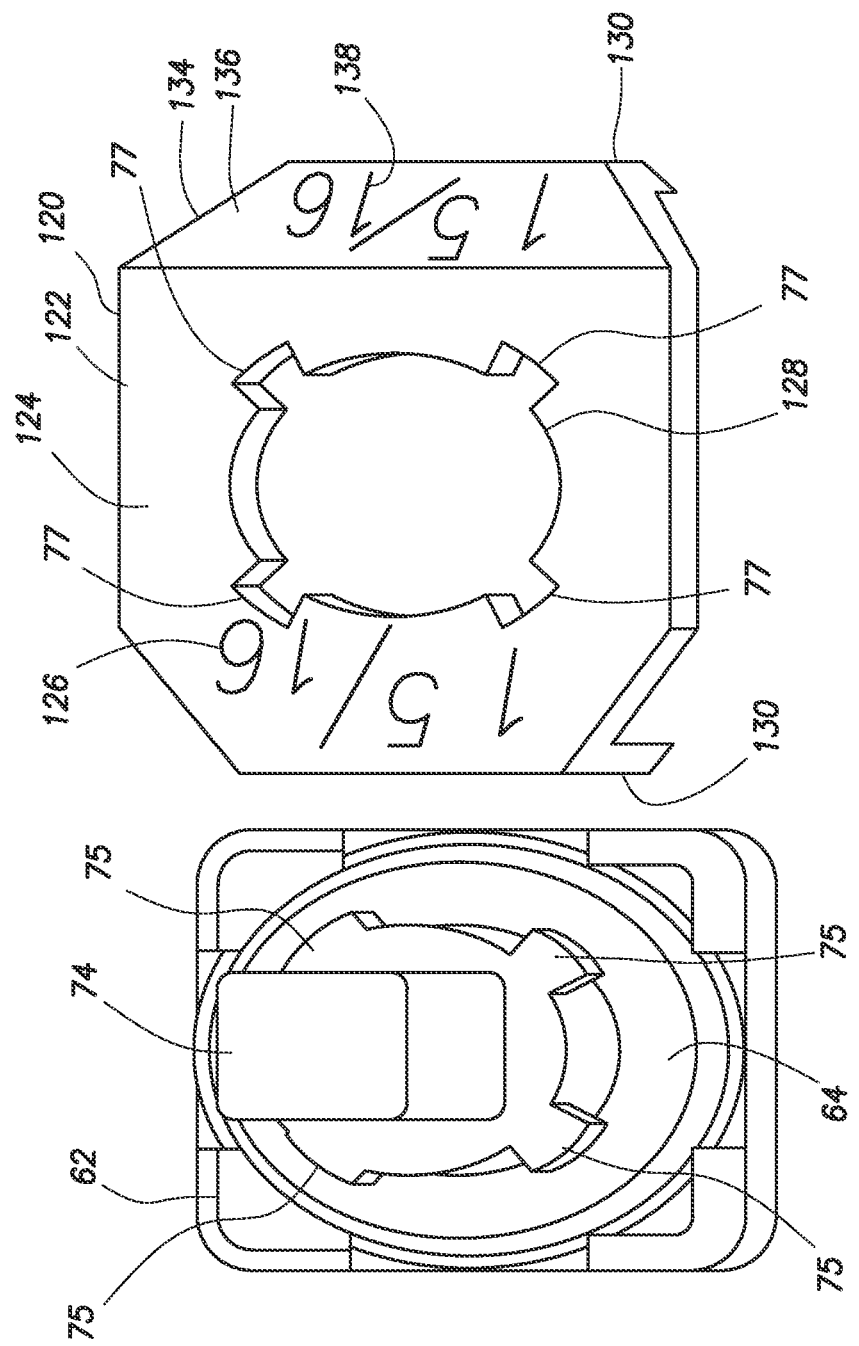
FIG. 12 is a top orthogonal view of an exemplary clip member and tabbed mounting post according to an aspect of the disclosure.

Best seen at FIG. 12 is an exemplary embodiment of a clip member 120 wherein the clip member 120 is attachable to a corresponding socket holder assembly 60, shown side by side with the clip member, at the mounting member 64. The clip members 120 can attach to the mounting post 74 or a columnar shoulder 78, at a plurality of tabs 75, for example. In an embodiment, each clip member is releasably attached to the mounting member 64 of a corresponding socket holder assembly 60. The clip members can attach by snap-on, slide-on, tongue and groove, or friction fit, as is known in the art. Alternately, the clip and mounting members can be formed monolithically. In an embodiment of a clip member which is releasably attached to the mounting member, the tabs 75 align with recesses 77 defined in the aperture 128 perimeter to allow lifting of the clip member 120 from the mounting member 64. Note that the mounting member 64 must be turned, here by a one-eighth turn, to align the tabs 75 and recesses 77 for placement or removal of the clip member from the post. Alternately, the clip member can employ a lip to engage a corresponding lip defined at the perimeter of the aperture 128, etc., as is known in the art.

As with the discussion of clip members above herein, each clip member 120 defines a central plate 122 defining a generally planar surface 124 which can be used for indicia 126, an aperture 128, and opposing legs 130. Note that neither the clip flanges 132 nor the corresponding rail grooves 46 are necessary since the clip members attach to the mounting member 64 rather than the rail assembly body 14. In an embodiment, an angled plate 134 having an angled surface 136 for indicia 138 extends from a side of the central plate 122 at an angle of between 10 and 90 degrees with respect to the generally planar surface of the plate. In alternate embodiments, the clip member 120 can comprise a central plate 122 with or without a single leg 130 or single angled plate 126. Clip members can attach to the mounting member or to the rail assembly in the various embodiments thereof described.

Dimensionality

Whether the clip members are attachable to the mounting posts or the rail assembly, they can be provided in sets. In an embodiment, a set of clip members is provided wherein either: each clip member has indicia different from all other clip members; or two or more clip members have identical indicia (i.e., for the user having more than one socket of a given size). In an embodiment, multiple sets of clip members are provided wherein a first set of clip members has indicia indicating various sizes of socket of a first type, and wherein a second set of clip members has indicia indicating sockets of various sizes of a second type. Types of sockets include shallow, deep, extra deep, impact, or swivel sockets.

The clip members are, in some embodiments, interchangeable across socket holders whether the clip members attach to the rail assembly or to the socket holders directly. Further, in some embodiments, the socket holders and/or clip members are removable from the rail assembly and can be rearranged by a user, such as to provide an arrangement of holders and clip members suitable to the sockets the user owns and/or the arrangement of sockets he prefers. That is, the user can remove clip members with indicia for sockets he does not have, add multiple clip members with identical indicia for multiple sockets of the same size, arrange the sockets by size then type (or vice versa), etc.

Modular Clip System

Figure 13:
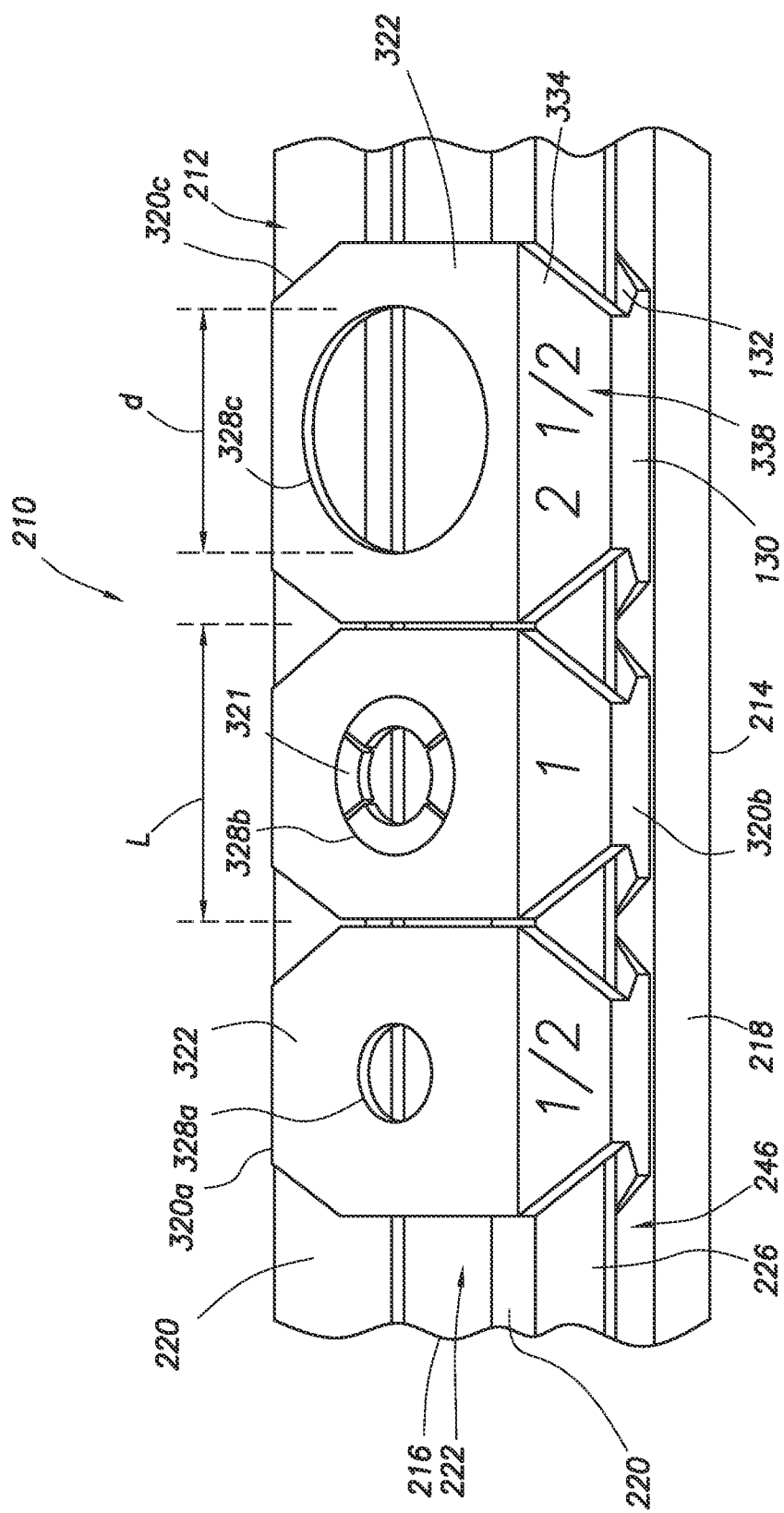
FIG. 13 is an orthogonal view of an exemplary modular socket organization system according to an aspect of the disclosure, with end cap removed.

FIG. 13 is an orthogonal view of an exemplary modular socket organization system according to an aspect of the disclosure. A modular system 210 is presented having a socket rail assembly 212 and a plurality of clip members 320. The rail assembly 212 includes a generally hollow, longitudinally extending rail body 214 defining an interior channel 222 into which sockets 5 can be positioned. Cooperating clip members 320 slidingly engage the rail assembly body 214 and define apertures 328 through which sockets 5 can be positioned. Briefly, the rail assembly can include end caps, a back plate assembly, a magnetic plate, a body 214 with bottom wall 216, side walls 218, flanges 220, angled walls 226, interior channel 222, and opposed open ends, etc., similar to those described in relation to other embodiments above.

Briefly, the clip members 320 are generally of similar design to those described above. An exemplary clip member 320 has a central plate 322 defining a generally planar surface for indicia, a pair of opposed legs 330 which may also bear indicia, and an aperture 328 for engaging a socket 5. The clip members 320 can include angled plates 334 with a surface for indicia 338. The clip members 320 cooperate with corresponding features on the rail assembly as described above. The clip members 320 can slide onto the body 214 or can snap-on to the rail assembly 212 as described elsewhere herein.

In an embodiment, each clip member 320 further includes a socket holding mechanism 321 such as an o-ring, gasket, split gasket, or other friction fit device defined by or attached to the perimeter of the aperture 328 for grippingly engaging a socket 5 positioned through the aperture 328.

Alternately or additionally, an embodiment includes a magnetic plate 323 at or comprising the bottom wall 216 of the rail assembly for magnetically holding sockets 5 to the assembly. The magnetic surface can be a magnetic strip attached to the rail assembly by fastener, adhesive, or otherwise as known in the art, or may form part of the rail assembly.

The apertures 328 of the plurality of clip members 320 are of varying diameter to accommodate and correspond to sockets of varying diameter. In a given set of sockets, there may be multiple small sockets of a uniform smaller diameter and a plurality of larger diameter sockets designed for driving larger headed fasteners, for example. Successively larger sockets may be provided to allow for driving successively larger fastener sizes.

The plurality of clip members 320 provide a plurality of aperture diameters for cooperation with the sockets of various diameter. For example, a set of socket-holding clip members 320 are provided wherein at least one clip member 320a defines an aperture of a first diameter 328a for accepting a socket of a coordinating diameter, at least one clip member 320b defines an aperture of a second diameter 328b for accepting a socket of a second coordinating diameter, and at least one clip member 320c defines an aperture of a third diameter 328c for accepting a socket of a third coordinating diameter.

In an embodiment, a set of clip members 320 is provided having at least one clip member 320 of each of three or more diameter apertures 328 for accepting sockets of at least three coordinating diameters. Further, each clip member 320 includes indicia on at least one surface thereof indicating the socket size coordinating with the clip member 320. In a further embodiment, indicia is provided on at least a surface of the central plate 322 of each clip member 320 and identical indicia is provided on at least one angled plate 326 or leg 330 of the clip member 320.

Each clip member 320 defines a longitudinal length, L, measured from opposing sides of the central plate 322. For sockets of particularly large diameter, clip members 320c are provided having a relatively greater length allowing for larger diameter apertures 328c. In the kits described above, one or more of such greater-length clip members may be provided.

The aperture 328 diameters, d, are measured at the perimeter of the aperture and may be nominally larger than the socket diameter for which it is designed. Where the aperture 328 employs a socket holding mechanism 321 such as a gasket, o-ring, or other friction-fit member, the aperture will be of greater diameter than the corresponding socket diameter to allow for the holding mechanism 32 while accepting the socket.

For specific examples, a typical set of sockets can comprise a number of sockets, which may be shallow, deep, extra deep, impact, or swivel sockets, and can be designed for use in driving 6 point, 12 point, spline, hex head, etc., fasteners. The drive end of a standard socket is one-quarter inch, although drive ends may vary and are available in three-eighths and one-half inch.

An exemplary set of sockets can be for use with ⅛ inch to ⅝ inch fasteners, in increments of thirty-seconds of an inch. A typical metric set of sockets may be for 6 mm to 15 mm fasteners by 1 mm increments. In a given set of sockets, there may be multiple sockets having the same diameter. For example, 4 mm through 9 mm shallow sockets may all have a base diameter of 12.1 mm. Sockets for larger size fasteners will have larger diameters. For example, a 15 mm shallow socket may have a 19.4 mm base diameter. Further, for a single size fastener it is possible to have sockets of differing diameters since a shallow socket may have a smaller diameter than a thick-walled impact socket. For example, a 9 mm shallow socket can have a base diameter of 12.1 mm whereas a 9 mm impact socket can have a base diameter of 14 mm.

The clip members for use with such socket sets can vary in length and aperture diameter as needed. Depending on the set of sockets, various combinations or sets of clips can be employed. Further, a kit of clips can be created by grouping together selected clip members having lengths, aperture diameters, and/or indicia corresponding to a set of sockets as well as a rail assembly. For example, a kit can comprise: a rail assembly; a number of sockets for ⅛ inch to ⅝ inch fasteners and having associated base diameters ranging from 7/16 inch to 25/32 inch; and a corresponding number of clip members, marked with corresponding size indicia, each of a length greater than the associated base diameter of the corresponding socket (e.g., by one-eighth to one-quarter inch), and each having an aperture of an effective diameter to position or hold the corresponding socket. Herein, effective diameter is meant to encompass aperture and/or gasket diameters adequate to position or hold the socket.

Each clip member 320 further includes a mechanism for sliding attachment to the rail assembly 212. In FIG. 13 each clip member 320 defines opposed flanges 332 which engage corresponding grooves 246 defined in the rail assembly 212. In an embodiment, the attachment mechanism will hold the clip member in a selected position unless a user pushes the clip member along the rail assembly. That is, the clip members will not simply slide along the rail assembly due to tilting of the system. For example, the flanges 332 may grippingly engage the groove 246 by friction fit or the flanges can define tabs which "snap" into corresponding indentations in the groove.

Alternate sliding attachments can be used such as where the clip members 320 (with or without opposed legs) define one or more attachment mechanisms extending from a surface thereof and for cooperating with corresponding attaching features on the rail assembly. For example, the clip members and rail assembly can define cooperating hooks, tabs and slots, tongue and groove, etc. The clip members 320 can include at least one leg 330 in various embodiments and/or at least one angled plate. In certain embodiments the opposed clip legs 330 or the central plate 322 can slidingly cooperate with or attach to an interior surface or flanges of the interior channel 222. These and other variations of sliding attachment mechanisms will be apparent to those of skill in the art and can be adopted or modified for use on the various socket holder assemblies presented herein.

While the making and using of various embodiments of the present disclosure are discussed in detail below, it is appreciated that the present disclosure provides many applicable concepts that may be embodied in a wide variety of specific contexts. The specific embodiments discussed herein are merely illustrative of specific ways to make and use the disclosure. Only the claims appended hereto delimit the scope of any claimed inventions.

It is claimed:

1. A socket organizer for releasably and adjustably holding a plurality of socket holders, the organizer comprising:
   a longitudinally extending rail assembly having a body defining an interior channel;
   a plurality of socket holders, each socket holder having a base member slidingly engaged within the interior channel of the rail assembly, and a rotationally movable mounting post for releasably holding a socket;
   each mounting post movable between a locked position in which a socket is held in place on the mounting post, and an unlocked position in which the socket is released from the socket holder; and
   each socket holder having a locking tab extending from the mounting post and engaging a cooperating slot defined in the base member, a recess defined in the slot, wherein the locking tab is positioned in the recess when the mounting post is in the locked position; and
   a socket holder positioning mechanism for securing socket holders at selected positions along the rail assembly, wherein the socket holder positioning mechanism further comprises:
     a plurality of laterally extending, longitudinally spaced-apart ridges extending along the rail assembly, and
     for each socket holder, at least one positioning tab extending from the socket holder base for selectively engaging the ridges.

2. The socket organizer of claim 1, wherein each positioning tab is movable between an engaged position, wherein engagement of the positioning tab and one of the plurality of ridges prevents longitudinal movement of the socket holder along the rail assembly, and an unengaged position, wherein the socket holder is free to slide longitudinally along the rail assembly.

3. The socket organizer of claim 1, wherein, for each socket holder, the mounting post is rotatably attached to the base member, and wherein the at least one positioning tab extends downwardly from the mounting post, the at least one positioning tab extending through and slidingly engaging a cooperating slot defined by the base member, the at least one positioning tab rotating between an engaged position, wherein engagement of one of the at least one positioning tabs and one of the plurality of ridges prevents longitudinal movement of the socket holder along the rail assembly, and an unengaged position, wherein the socket holder is free to slide longitudinally along the rail assembly.

4. The socket organizer of claim 3, wherein for each socket holder: the mounting post defines a pair of positioning tabs of the at least one positioning tabs, each of the pair of positioning tabs extending through and slidingly engaging the cooperating slot, the pair of tabs rotating between:
   a first engaged position wherein one of the pair of positioning tabs engages a ridge of the rail assembly;
   an unengaged position wherein the socket holder is free to slide longitudinally along the rail assembly; and
   a second engaged position wherein the other of the pair of positioning tabs engages a ridge of the rail assembly.

5. The socket organizer of claim 4, wherein rotational movement from the first engaged position to the second engaged position corresponds to one-quarter turn of the mounting post, and wherein movement from either the first or second engaged positions to the unengaged position corresponds to a one-eighth turn of the mounting post.

6. The socket organizer of claim 4, wherein a detent ball is engaged by a cam surface of the mounting post for moving the detent ball radially between a locked position in which a socket is held in place by the detent ball, and an unlocked position in which the socket is released from the socket holder.

7. The socket organizer of claim 6, wherein the socket holder's first and second engaged positions correspond to, respectively, the locked and unlocked positions of the detent ball.

8. The socket organizer of claim 6, wherein rotation of the mounting post one-quarter turn moves the detent ball between the locked and unlocked positions.

9. The socket organizer of claim 2, the rail assembly further comprising a longitudinally extending insert member slidingly cooperating with an insert channel defined along the rail assembly, and wherein the plurality of ridges are defined on the insert member.

10. The socket organizer of claim 1, further comprising a magnetic plate secured to the rail assembly for mounting the rail assembly on a ferrous surface.

11. The socket organizer of claim 1, wherein the rail assembly further comprises: an alignment mechanism which cooperates with corresponding alignment features defined on the base member of each socket holder, the alignment mechanism preventing insertion of the socket holder into an open end of the interior channel of the rail assembly unless the alignment feature and the alignment mechanism are cooperatively aligned.

12. The socket organizer of claim 11, wherein the alignment mechanism further comprises a shaped surface on a side or bottom wall of the rail assembly and wherein the aligning feature comprises a cooperating shaped surface on the base member.

13. A socket organizer for releasably and adjustably holding a plurality of socket holders, the organizer comprising:
   a longitudinally extending rail assembly having a body defining an interior channel;
   a plurality of socket holders, each socket holder having a base member slidingly engaged with the interior channel of the rail assembly, and a mounting post for releasably holding a socket;
   each mounting post rotationally movable between a locked position in which a socket is held in place on the mounting post, and an unlocked position in which the socket is released from the socket holder; and
   each socket holder having a locking tab engaging a cooperating slot, a recess defined in the slot, and wherein the locking tab is positioned in the recess when the socket holder is in the locked position;
   a socket holder positioning mechanism for securing socket holders at selected positions along the rail assembly, wherein the socket holder positioning mechanism further comprises:
      a plurality of longitudinally spaced-apart ridges extending from the rail assembly, and
      for each socket holder, at least one positioning tab selectively movable into an engaged position in which the positioning tab engages at least one of the ridges.

14. The socket organizer of claim 13, wherein when the positioning tab is in the engaged position, the locking tab is in the locked position.

15. The socket organizer of claim 13, wherein the positioning tab extends downwardly and the plurality of cooperating ridges extend upwardly into the interior channel.

16. A socket organizer for releasably and adjustably holding a plurality of socket holders, the organizer comprising:
   a longitudinally extending rail assembly having a body defining an interior channel;
   a plurality of socket holders, each socket holder having a base member slidingly engaged within the interior channel of the rail assembly, and a mounting post for releasably holding a socket;
   each mounting post rotationally movable between a locked position in which a socket is held in place on the mounting post, and an unlocked position in which the socket is released from the socket holder; and
   wherein the rail assembly further comprises an alignment mechanism which cooperates with a corresponding alignment feature defined on the base member of each socket holder, the alignment mechanism and alignment feature cooperating to prevent:
      insertion of the socket holder into an open end of the interior channel of the rail assembly unless the alignment feature and the alignment mechanism are cooperatively aligned; and
      rotation of the base member once positioned on the rail assembly.

17. The socket organizer of claim 16, wherein the alignment mechanism further comprises a shaped surface on a side or bottom wall of the rail assembly and wherein the aligning feature comprises a cooperating shaped surface on the base member.

* * * * *